United States Patent [19]
Fujino

[11] Patent Number: 5,500,111
[45] Date of Patent: Mar. 19, 1996

[54] BACTERIA SUPPORTING MEDIUM, ESPECIALLY USEFUL FOR PRETREATMENT OF WASTE WATER

[76] Inventor: Yasuo Fujino, 1-700 Yoshino 170., Katsuyama-shi; Fukui-Ken, Japan

[21] Appl. No.: 184,148

[22] Filed: Jan. 21, 1994

[30] Foreign Application Priority Data

Jan. 22, 1993 [JP] Japan .................................. 5-027477

[51] Int. Cl.⁶ .................................................... C02F 3/10
[52] U.S. Cl. ........................ 210/150; 210/493.4; 210/496
[58] Field of Search ..................... 210/615, 150, 210/151, 493.1, 493.4, 494.1, 496, 497.1

[56] References Cited

U.S. PATENT DOCUMENTS

| | | | |
|---|---|---|---|
| 4,242,460 | 12/1980 | Chick et al. | 210/497.1 |
| 4,422,930 | 12/1983 | Hatanaka | 210/615 |
| 4,680,111 | 7/1987 | Veda | 210/615 |
| 4,717,519 | 1/1988 | Sagami | 210/615 |
| 4,729,828 | 3/1988 | Miller | 210/150 |
| 4,877,527 | 10/1989 | Brownell | 210/496 |
| 5,168,058 | 12/1992 | Bohak et al. | 210/150 |

FOREIGN PATENT DOCUMENTS 64-34496  2/1989  Japan ................................ 210/615

Primary Examiner—Thomas Wyse

[57] ABSTRACT

A bacteria-supporting medium of synthetic resin has a spiral shape with a relatively small pitch, and comprises plural S-shaped portions continuous with each other and defined at outer boundarios by a continuous winding line. Each S-shaped portion extends radially, and includes an upwardly-expanding part and a downwardly-expanding part. These parts are tapered toward a central opening.

15 Claims, 4 Drawing Sheets

BACTERIA SUPPORTING MEDIUM, ESPECIALLY USEFUL FOR PRETREATMENT OF WASTE WATER

FIELD OF THE INVENTION

This invention relates to a bacteria supporting medium, or an object on which to load bacteria, and more particularly relates to such a medium of a special shape.

BACKGROUND OF THE INVENTION

Polluted water can be purified by using such natural substances as sand or pebbles or by using an artificial filter comprising charcoal, filter paper, sponge or the like. In recent times we also use bacteria for that purpose. That is, we can encourage the growth of bacteria in a treating tank or introduce them from outside into the tank in order for them to attack the organic material in the polluted water and decompose it quickly. Of the various bacteria, Thiobacillus ferrooxidans is very unique. This bacteria oxidize ferrous iron ions in the water to ferric iron ions. The bacteria are called "chemoautotrophic bacteria" in microbiology. In addition to the above function, it oxidizes sulfur to sulfuric acid. This is a geomicrobiologically important function.

On the other hand, in the modern world the waste water discharged from factories, mines, refineries, and other industrial places, as well as from households, reaches a vast quantity. So sewage treatment is a very serious social problem in most need of attention. In particular, the waste water from mines contains, among others, such metals as iron, copper, and zinc. Then, it is economically important whether the iron contained in it is mostly ferrous iron or ferric iron. Where the iron is mostly ferrous iron, slaked lime is usually used to neutralize the water to pH 7 or 8, so that the ferrous iron settles. However, where the iron is ferric iron, ph 3 or 4 is sufficient to settle the iron and, therefore, fine powder of limestone can be used to neutralize the water to that value. Then, since limestone is about a third or fourth the price of slaked lime, changing the iron to ferric iron is an expedient step for an economical treatment of polluted water where the iron contained in it is ferrous iron. As described before, bacteria called "Thiobacillus ferrooxidans" oxidize ferrous iron to ferric iron, and so it has been in use for an economical treatment of polluted water containing a large amount of ferrous iron. The bacteria are loaded on a wool-like, netlike, or scrub-brush-like bacteria-supporting medium, and a number of such media are introduced into an oxidizing tank.

The conventional supporting medium, however, has a drawback that its surface area on which to load the bacteria is relatively small. Another drawback is that the solids in waste water are apt to get into the medium and stay there. A third drawback is that relatively large spaces, into which no portions of the media project, may exist between the media and, therefore, the polluted water may not be treated sufficiently. A fourth drawback contrasts with the third one. That is, if such flow passages are not formed between the media, then on the contrary the media may come into contact with each other at their surfaces. The fourth drawback also results in insufficient treatment of the water.

SUMMARY OF THE INVENTION

Accordingly it is the object of the invention to provide a bacteria-supporting medium which is free from the foregoing drawbacks of the conventional medium.

DETAILED DESCRIPTION OF PREFERRED EMBODIMENT

Figure 1:
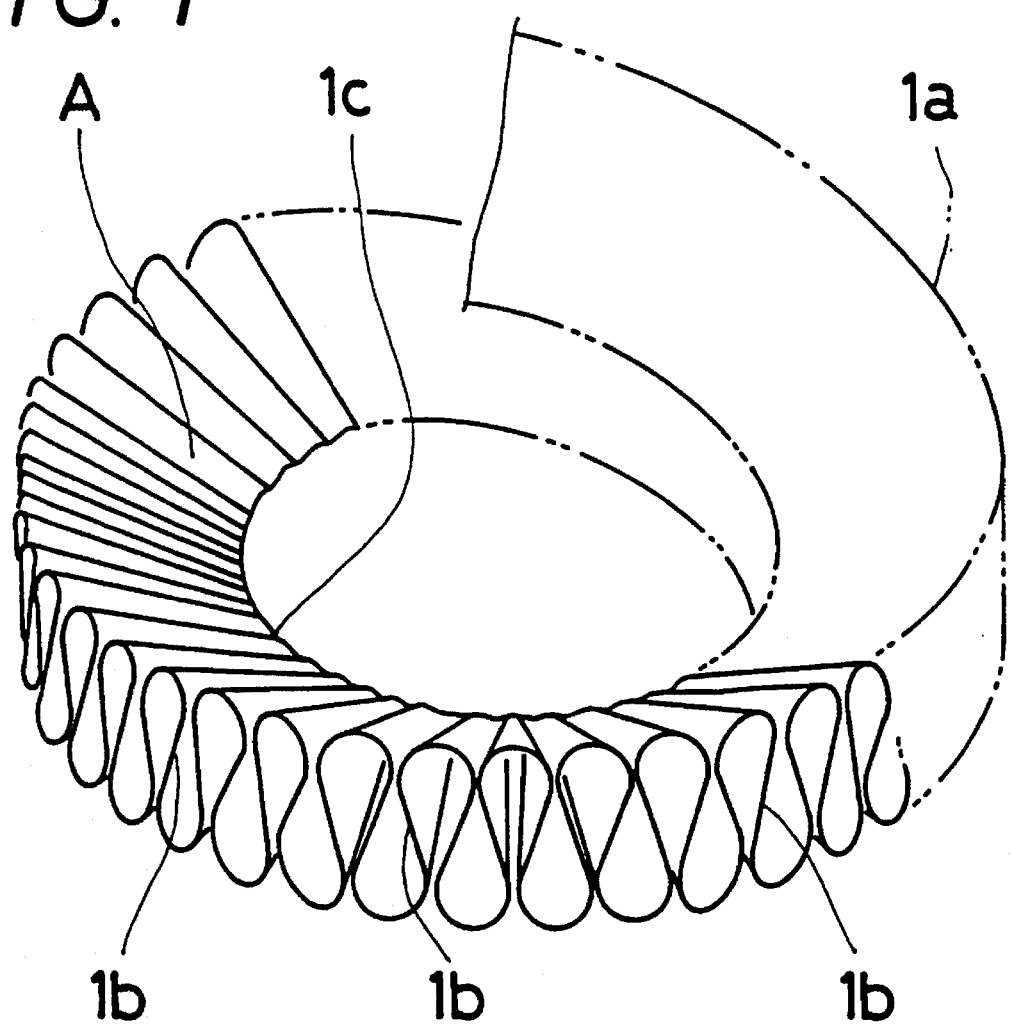
FIG. 1 shows a portion of a bacteria-supporting medium of the invention.
Figure 2:
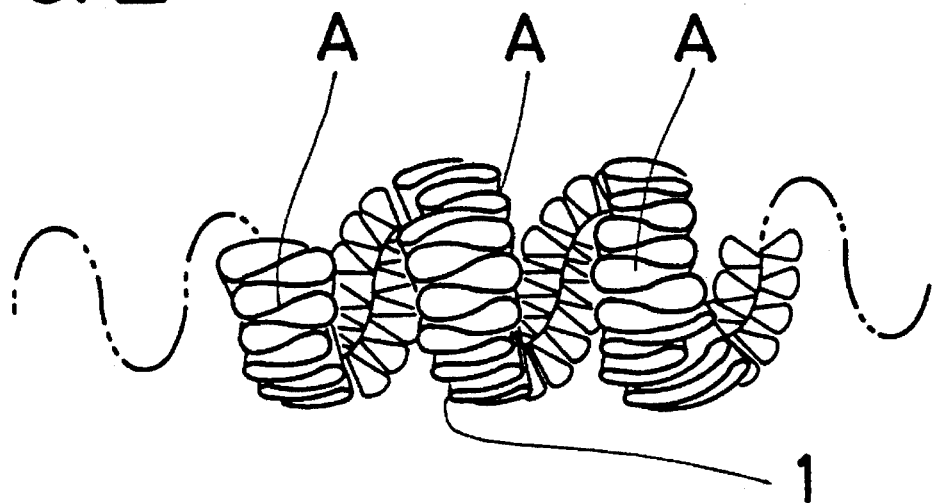
FIG. 2 shows the whole of the supporting medium.
Figure 3:
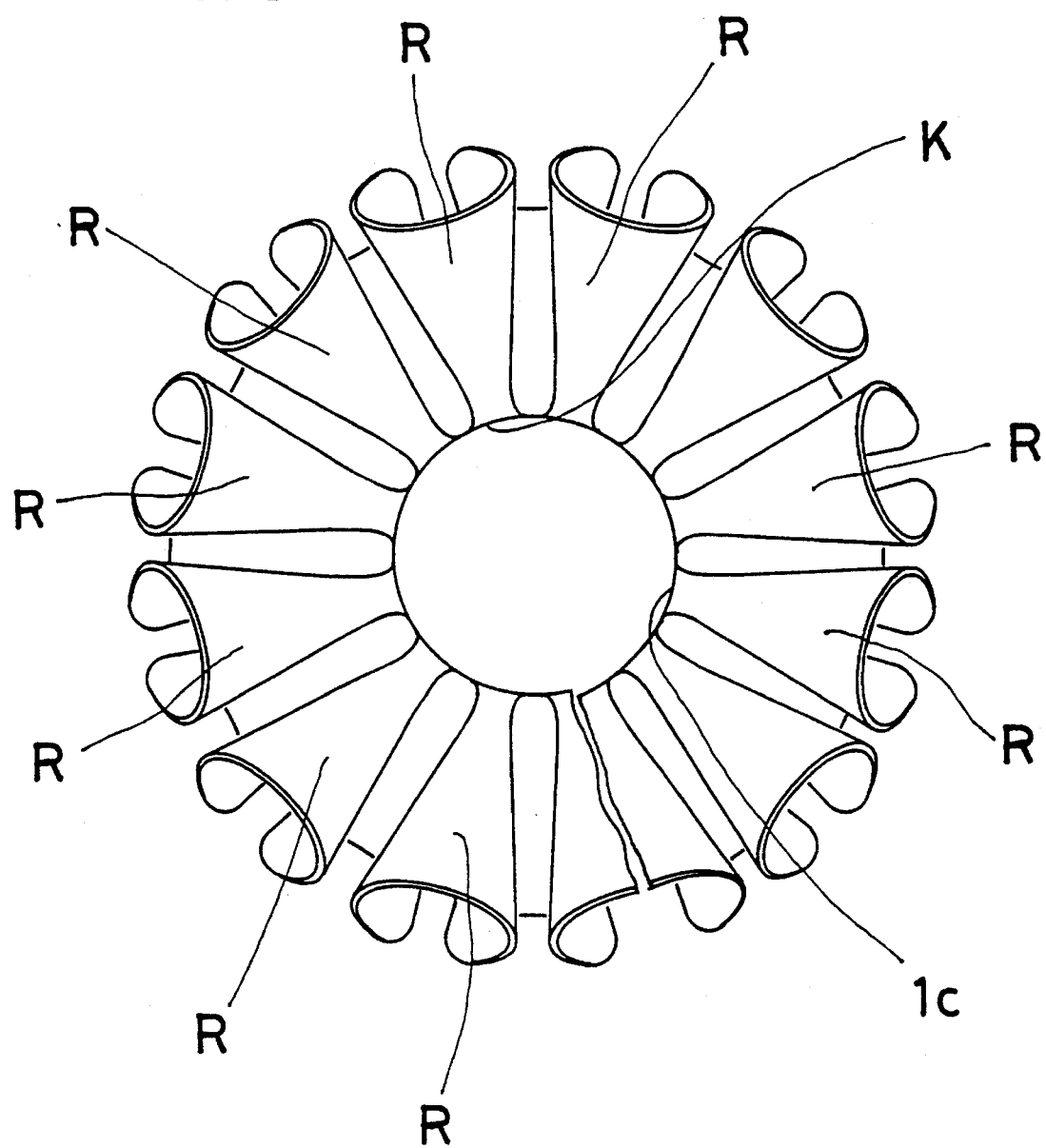
FIG. 3 is an enlarged plan view of a portion of the supporting medium.

As shown in FIG. 2, a bacteria-supporting medium of the invention has a spiral shape. It is made of synthetic resin. FIG. 1 shows a portion of the medium. As clearly shown in FIG. 1, the medium comprises numerous winding, or S-shaped, portions. All the S-shaped portions are continuous with each other, and are defined at their outer boundaries by a continuous winding line S. As clearly shown in FIGS. 1 and 3, the medium has a central opening K. Each S-shaped portion extends in a radial direction.

Figure 4:
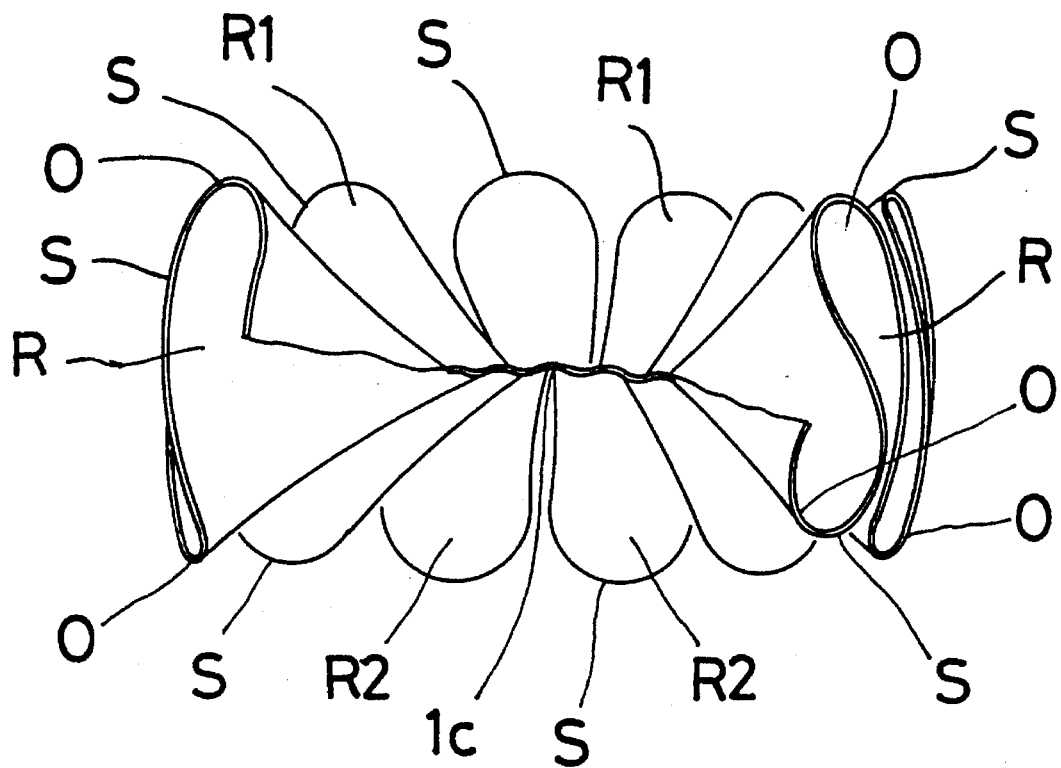
FIG. 4 shows a portion of the medium as viewed from its inner circumference toward its outer circumference.
Figure 4:
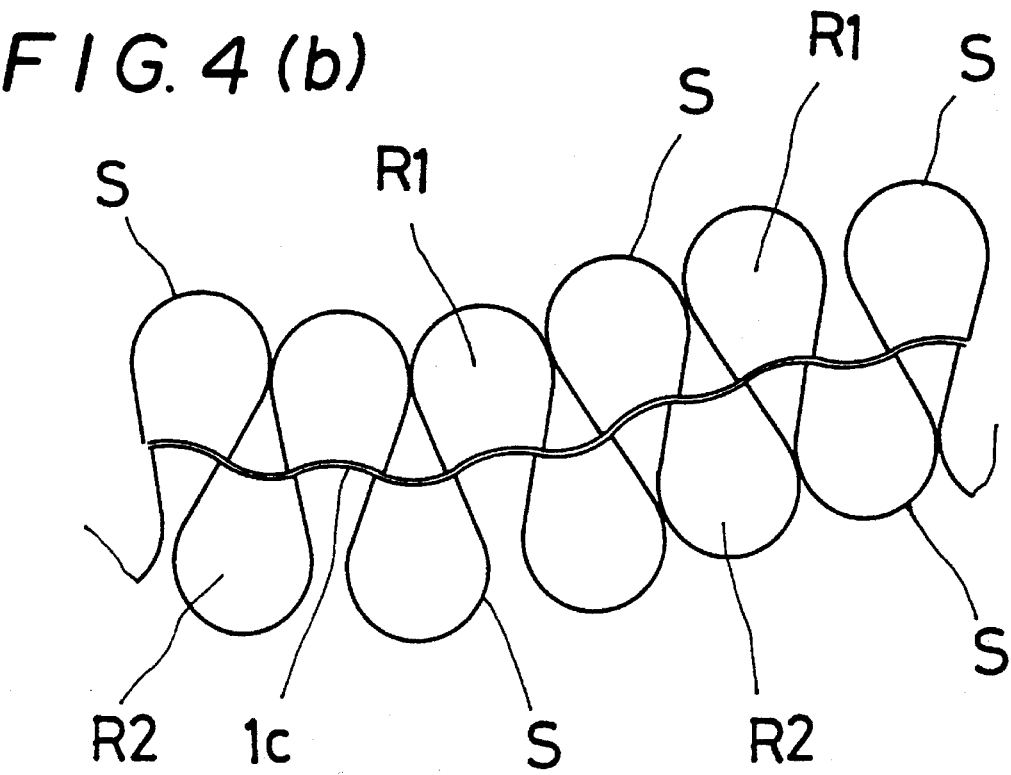

Each S-shaped portion includes an upwardly-expanding part R1 and a downwardly-expanding part R2. Each expanding part is tapered inwardly. As best shown in FIG. 4(a), one portion O of the upwardly-expanding part R1, as well as one portion O of the downwardly-expanding part R2, slightly bulges out. At the same time, as shown in FIG. 4(b), if the continuous winding line S is divided by an inner circumferential line 1c, its upper and lower segments are offset slightly.

Figure 5:
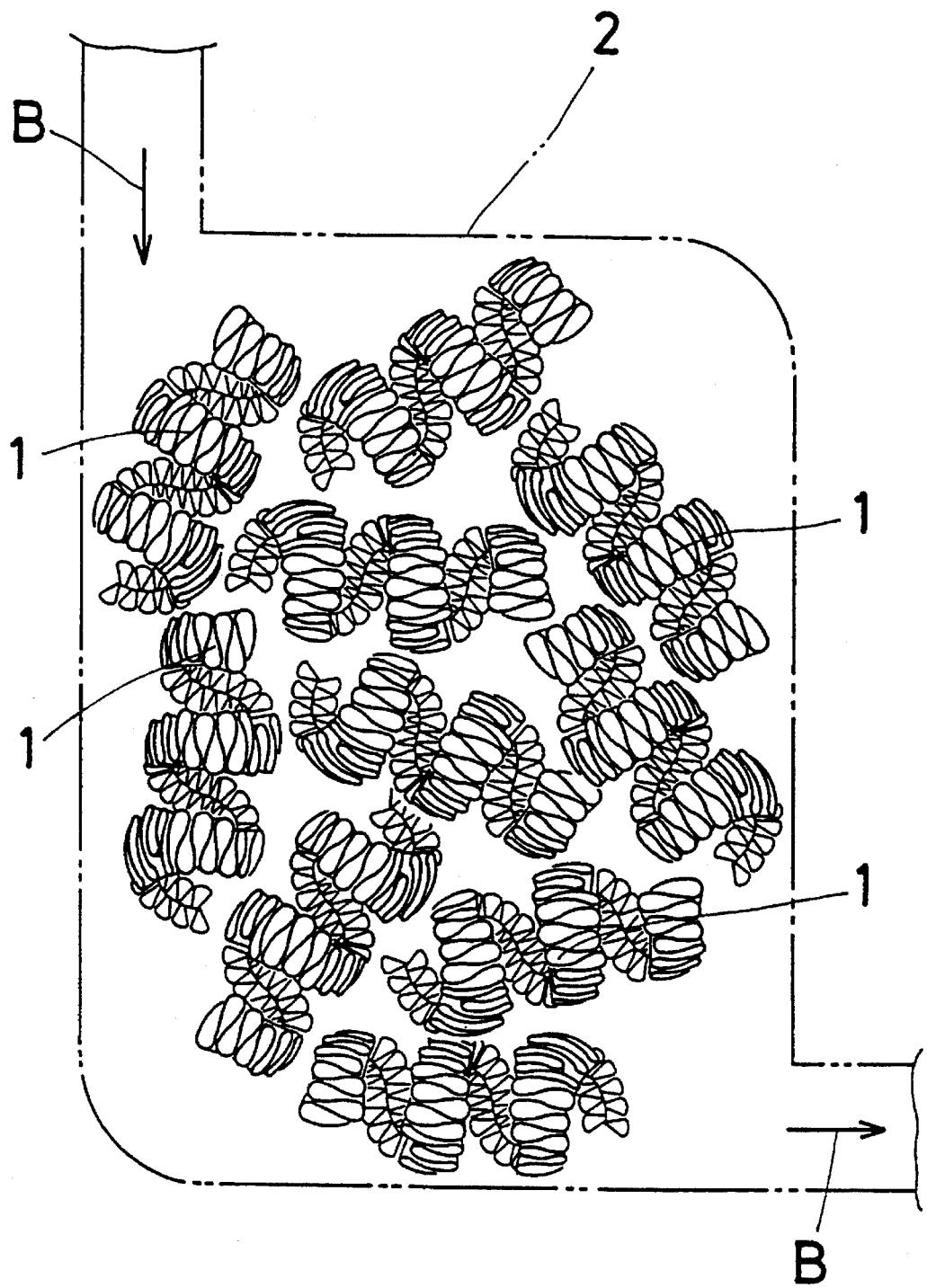
FIG. 5 shows plural media in a treating tank.

In use, bacteria, such as Thiobacillus ferrooxidans, are loaded on the medium, and plural such media are put into a treating tank 2 (FIG. 5). Then, polluted water to be treated is supplied into the tank 2. The medium of the invention has a treating surface area more than 10 times as large as the conventional medium. So the water is treated much more effectively. In addition, it will be appreciated that the medium of the invention has such a shape as does not allow solids in the water to accumulate in quantities in the medium. Also, since the pitch of its spiral shape is relatively small, flow passages not interrupted by anything are not readily formed between the media and, therefore, the water is treated sufficiently. At the same time, for the same reason, if the media move very close to each other, flow passages sufficiently large to treat the water remain.

After treatment in the tank 2, the water can be further treated with, for example, a suitable neutralizing agent.

What is claimed is:

1. A bacteria-supporting medium of synthetic resin which has a spiral shape with a relatively small pitch and comprises plural S-shaped portions continuous with each other and defined at outer boundaries by a continuous winding line, each of said S-shaped portions extending radially and including an upwardly-expanding part and a downwardly-expanding part, said upwardly-extending and downwardly-extending parts being tapered toward a central opening, one portion of said upwardly-expanding part, as well as one portion of said downwardly-expanding part, slightly bulging out, and upper and lower segments of said winding line being offset slightly upon dividing said winding line by an inner circumferential line.

2. A bacteria-supporting medium as recited in claim 1, wherein said medium is a continuous, substantially planar, undulating surface, wound in a spiral.

3. The bacteria supporting medium recited in claim 2, wherein said S-shaped portions of said substantially planar medium extend radially outwardly from a central portion of the spiral.

4. The bacteria supporting medium recited in claim 3, wherein undulations of said S-shaped portions have unequal magnitudes at inner and outer regions along said spiral.

5. The bacteria supporting medium recited in claim 4, wherein the magnitude of undulation along an outer region along said spiral is larger than the magnitude of undulation along an inner region along said spiral.

6. In a bacteria supporting structure of synthetic resin which has a spiral shape with a relatively small pitch and comprises plural S-shaped portions continuous with each other and defined at outer boundaries by a continuous winding line, each of said S-shaped portions extending radially and including an upwardly-expanding part and a downwardly-expanding part, said upwardly-extending and downwardly-extending parts being tapered toward a central opening, one portion of said upwardly-expanding part, as well as one portion of said downwardly-expanding part, slightly bulging out, and upper and lower segments of said winding line being offset slightly upon dividing said winding line by an inner circumferential line, a spirally wound planar medium forming said spiral shape as a spiral having a plurality of windings, each winding of said spiral including a plurality of S-shaped undulations of said medium forming said S-shaped portions of the structure.

7. The bacteria supporting structure recited in claim 6, wherein each of said S-shaped undulations is tapered expansively from a radially inward portion of a winding of said spiral to a radially outward portion of said winding of said spiral to form said radially extending S-shaped portions.

8. The bacteria supporting structure recited in claim 7, wherein said continuous winding line comprises, along each winding of said spiral, a first continuous winding line formed by said plurality of expansively tapered S-shaped undulations along said radially outward portion of said winding and a second continuous winding line formed by said S-shaped undulations along said radially inward portion of said winding, and wherein said second continuous winding line divides said first continuous winding line into upper and lower segments offset from one another.

9. The bacteria supporting structure recited in claim 7, wherein each of said S-shaped undulations includes upper and lower portions relative to a respective winding of the spiral forming said upwardly-expanding and downwardly-expanding parts of said S-shaped portions, each of said upper and lower portions of said S-shaped undulation having a portion bulging transversely of a radius of a winding of the spiral and transversely of an axis of the spiral.

10. The bacteria supporting structure recited in claim 7, wherein said structure comprises a plurality of separate, spirally would planar media, each separate spirally wound planar medium having a plurality of windings each winding including a plurality of said S-shaped undulations.

11. The bacteria supporting structure recited in claim 6, wherein said planar medium includes substantially parallel first and second edges, said windings of said spiral having a substantially common radius, and said first edge forming a radially inward portion of each winding of said spiral and said second edge forming a radially outward portion of each winding of said spiral.

12. The bacteria supporting structure recited in claim 11, wherein each of said S-shaped undulations is tapered expansively from said radially inward portion of a winding of said spiral to said radially outward portion of said winding of said spiral to form said radially extending S-shaped portions.

13. The bacteria supporting structure recited in claim 12, wherein said continuous winding line comprises, along each winding of said spiral, a first continuous winding line formed by said plurality of expansively tapered S-shaped undulations along said radially outward portion of said winding and a second continuous winding line formed by said S-shaped undulations along said radially inward portion of said winding, and wherein said second continuous winding line divides said first continuous winding line into upper and lower segments offset from one another.

14. The bacteria supporting structure recited in claim 12, wherein each of said S-shaped undulations includes upper and lower portions relative to a respective winding of the spiral forming said upwardly-expanding and downwardly-expanding parts of said S-shaped portions, each of said upper and lower portions of said S-shaped undulation having a portion bulging transversely of the radius of a winding of the spiral and transversely of an axis of the spiral.

15. The bacteria supporting structure recited in claim 12, wherein said structure comprises a plurality of separate, spirally wound planar media, each separate spirally wound planar medium having a plurality of windings each winding including a plurality of said S-shaped undulations.

\* \* \* \* \*